United States Patent [19]
Rubin

[11] Patent Number: 5,169,858
[45] Date of Patent: Dec. 8, 1992

[54] ANTI-TUMOR COMPOSITIONS CONTAINING THE REACTIVE PRODUCT OF BENZALDEHYDE OR SALICYLALDEHYDE WITH PENICILLAMINE AND METHOD OF USE THEREOF

[76] Inventor: David Rubin, 4173 Camino Ticino, San Diego, Calif. 92122

[21] Appl. No.: 833,801

[22] Filed: Feb. 26, 1986

Related U.S. Application Data

[63] Continuation-in-part of Ser. No. 682,991, Dec. 18, 1984, abandoned.

[51] Int. Cl.$^5$ .......................................... A61K 31/425
[52] U.S. Cl. ................................. 514/365; 548/201
[58] Field of Search ......................... 514/365; 548/201

[56] References Cited

U.S. PATENT DOCUMENTS 4,384,001  5/1983  Gosalvez ............................ 514/365

FOREIGN PATENT DOCUMENTS

| | | | |
|---|---|---|---|
| 2951050 | 7/1980 | Fed. Rep. of Germany ...... | 514/365 |
| 55-167220 | 12/1980 | Japan ................................. | 514/365 |
| 56-33216 | 10/1981 | Japan ................................. | 514/365 |
| 57-128625 | 8/1982 | Japan ................................. | 514/365 |

OTHER PUBLICATIONS

Brugarolas, A. et al., "Treatment of Cancer by an Inducer of Reverse Transformation," *Lancet* 1980, 1 (8159), 68–70; (Chem. Abstract No. 92:157869n).
Terol, A. et al., *Eur. J. Med. Chem.-Chimica Therapeutica*, 13, 2, 149–151 (1978).
Oehler, E. et al., *Chem. Ber.* 112, 107–115 (1979).
Paul, B. et al., *Journal of Medicinal Chemistry*, 1976, vol. 19, No. 8, 1002–1007.

*Primary Examiner*—Floyd D. Higel
*Attorney, Agent, or Firm*—Browdy and Neimark

[57] ABSTRACT

A composition for therapy of tumors having high tyrosinase activity contains the reaction product of penicillamine with a cytotoxic aldehyde, or pharmaceutically acceptable salts or esters thereof, and a pharmaceutically acceptable vehicle. The preferred compounds are 5,5-dimethyl-2-phenyl-4-thiazolidine carboxylic acid or 5,5-dimethyl-2-(2-hydroxyphenyl)-4-thiazolidine carboxylic acid, or pharmaceutically acceptable salts or esters thereof. Treatment preferably comprises an intra-arterial drip. Diagnosis of tumors suitable for treatment by means of these compositions may be accomplished by administering a radioactive copper salt and scanning for accumulations of radioactivity. This will indicate sites of high tyrosinase activity.

14 Claims, No Drawings

ANTI-TUMOR COMPOSITIONS CONTAINING THE REACTIVE PRODUCT OF BENZALDEHYDE OR SALICYLALDEHYDE WITH PENICILLAMINE AND METHOD OF USE THEREOF

CROSS-REFERENCE TO RELATED APPLICATION

The present application is a continuation-in-part of application Ser. No. 682,991, filed Dec. 18, 1984, now abandoned the entire contents of which are hereby incorporated by reference.

FIELD OF INVENTION

The present invention relates to an improved method and composition for cancer therapy, and an improved composition therefor, and, more particularly, to such a method and composition for the therapy of tumors which have substantial copper concentrations.

BACKGROUND OF THE INVENTION

Benzaldehyde has been shown to have anti-tumor activity. See Kochi, M. et al, "Anti-Tumor Activity of Benzaldehyde," *Cancer Treat. Rep.*, 64(1) 21–3, January 1980. It is theorized that benzaldehyde has such anti-tumor activity because it acts very strongly and immediately with cysteine. Since fast growing cells require more cysteine than normal cells, treatment with benzaldehyde will theoretically interfere with fast multiplication of tumor cells without being unduly threatening to normal cells. Also, leucotriene-$D_4$, which is essential for cell multiplication, is a conjugate of arachidonic acid with cysteine. It is believed that by depriving the body of cysteine, multiplication of new cells is suppressed.

Other aldehydes, much as salicylaldehyde, formaldehyde, glutaraldehyde, and others, also have caustic and cytotoxic properties.

Penicillamine (dimethylcysteine) has known therapeutic utility. One property of penicillamine is its ability to form complexes with copper and remove it from the body. Thus, penicillamine is commonly used for the treatment of diseases caused by excess copper, e.g., Wilson's Disease.

Some tumors are known to show high tyrosinase activity. Tyrosinase is a metallo enzyme and requires copper. Tyrosinase can thus be inhibited by removing copper.

SUMMARY OF THE INVENTION

It is an object of the present invention to enhance the anti-tumor activity of benzaldehyde.

It is another object of the present invention to eliminate the caustic activity of benzaldehyde when used in anti-tumor therapy.

It is an further object of the present invention to concentrate benzaldehyde in the body at the site of malignant tumors.

It is yet another object of the present invention to combine benzaldehyde with penicillamine to get the benefit of both and eliminate the disadvantages of the caustic activity of benzaldehyde.

It is still a further object of the present invention to provide a method to diagnose tumors treatable by means of the compounds of the present invention.

It is another object of the present invention to provide a method for the early diagnosis of certain types of tumors, including melanoma and mammary carcinoma.

It is still another object of the present invention to combine salicylaldehyde with penicillamine to get an improved anti-tumor agent for the treatment of certain types of tumors.

It is yet a further object of the present invention to combine other cytotoxic aldehydes with penicillamine to obtain an anti-tumor agent for the treatment of tumors with high tyrosinase activity.

These and other objects of the present invention are obtained by reacting a cytotoxic aldehyde with penicillamine. For example, when benzaldehyde and penicillamine are reacted with one another, 5,5-dimethyl-2-phenyl-4-thiazolidine carboxylic acid is formed in accordance with the following reaction:

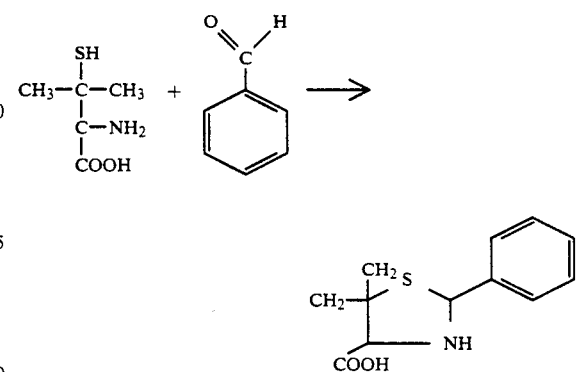

A pharmaceutical composition may be formed based on 5,5-dimethyl-2-phenyl-4-thiazolidine carboxylic acid as the active principle and administered to mammals for cancer therapy and particularly for therapy of tumors which have substantial copper concentrations.

The outstanding properties of 5,5-dimethyl-2-phenyl-4-thiazolidine carboxylic acid are based on the fact that this reaction product of benzaldehyde and penicillamine retains the anti-tumor properties of both of the reactants and synergistically improves the effectiveness of both and eliminates any disadvantages.

As disclosed in U.S. Pat. No. 4,762,705 penicillamine alone has anti-tumor activity because of its property of chelating with copper. The enzyme tyrosinase requires copper for its activity. It has been reported that many types of tumors, such as melanoma and breast carcinoma, have unusually high levels of tyrosinase activity. Since tyrosinase has the effect of denaturing interferon, the normal bodily production of this substance will be neutralized, thus diminishing the body's ability to fight the tumor cells. As penicillamine chelates with the copper, needed by tyrosinase for its activity, it essentially deactivates this tyrosinase activity; this permits the normal bodily interferon to resume its battle against the tumor cells, and also permits the administration of interferon to become effective. Without eliminating the tyrosinase activity of the tumors, added interferon cannot serve its intended function.

Benzaldehyde is an effective anti-tumor compound because it reacts very strongly and immediately with cysteine and will therefore interfere with fast multiplication of the tumor cells. Benzaldehyde, however, is very caustic and will have some amount of side effects on normal cells which also include cysteine. Utilization of the reaction product of benzaldehyde and penicillamine in accordance with the present invention will eliminate these disadvantages as the reaction product, having no free aldehyde groups, is not caustic as is benzaldehyde. Additionally, the reaction product of benzaldehyde and penicillamine retains the ability of penicillamine to chelate with copper. One difference, however, is that free 5,5-dimethyl-2-phenyl-4-thiazolidine carboxylic acid and the copper chelate with penicillamine are water-soluble while the copper chelate with 5,5-dimethyl-2-phenyl-4-thiazolidine carboxylic acid is water insoluble. This difference is a distinct advantage since the active compound will precipitate at the cancer site where it chelates with the copper thereat. Thus, it is deposited where it is needed. Elsewhere, where there is no copper, it will remain water-soluble and be flushed from the body. Due to the effect of precipitation of the compound at the site of tumors which have great tyrosinase activity and therefore great amounts of copper, the compound will be targeted directly to the tumor cells. Furthermore, once the compound chelates with copper at the cancer site, it becomes substantially more labile, permitting hydrolysis of the 5,5-dimethyl-2-phenyl-4-thiazolidine carboxylic acid and thus release of benzaldehyde which then regains its activity against cysteine and asserts its anti-tumor effect directly at the place where it is most needed. The remaining penicillamine-copper chelate will become water soluble and be flushed from the area, thus deactivating the tyrosinase activity at the cancer site, which deactivation has its own anti-tumor effect.

Another aspect of the present invention involves the substitution of other cytotoxic aldehydes, or aldehydes which break down to other cytotoxic compounds, for benzaldehyde in order to produce other reaction products with penicillamine which can be used in the same manner as 5,5-dimethyl-2-phenyl-4-thiazolidine carboxylic acid discussed above. Any aldehyde which will have a toxic effect of any kind at a tumor site may be used in accordance with the present invention. Such aldehydes may include aliphatic aldehydes, such as formaldehyde, dialdehydes, such as glutaraldehyde, and aromatic aldehydes, including phenyl aldehydes in which the phenyl group is substituted with one or more moieties such as Cl, Br, I, $NO_2$ and OH. Reacting any such aldehyde with penicillamine will effectively detoxify the compound, by eliminating the aldehyde group. The penicillamine portion of the reaction product will cause the reaction product to chelate with copper and eventually hydrolyze at the site of tumors with high tyrosinase activity, and thus a substantial presence of copper, thereby serving as a form of "magic bullet" to release the aldehyde only at the tumor site. Since the aldehyde is itself toxic to the tumor cells upon contact, and since penicillamine deactivates tyrosinase activity, the reaction products of the present invention are effective anti-tumor agents against those tumors having substantial tyrosinase activity.

One such aldehyde is salicylaldehyde. When substituted for benzaldehyde in the above-described reaction with penacillamine, 5,5-dimethyl-2-(2-hydroxypheny)-4-thiazolidine carboxylic acid is produced. This compound also has beneficial effects against tumors having high tyrosinase activity, as discussed above with respect to the 5,5-dimethyl-2-phenyl-4-thiazolidine carboxylic acid. The penicillamine part of the molecule will cause the drug to accumulate at the cancer site where there is a high amount of copper present. Salicylaldehyde is easily converted to salicylic acid which is known to be caustic and used, for example, against external warts. This compound also is cytotoxic to tumor cells when deposited thereat. The same dosages and modes of administration discussed for the 5,5-dimethyl-2-phenyl-4-thiazolidine carboxylic acid applies to the use of 5,5-dimethyl-2-(2-hydroxyphenyl)-4-thiazolidine carboxylic acid and the reaction products of penicillamine with aldehydes other than benzaldehyde and salicylaldehyde.

Another aspect of the present invention relates to the diagnosis of tumors which may be treatable by the compounds of the present invention. This may be done by administering a copper salt bearing a radioactive isotope of copper. Because of the high concentrations of copper at tumor sites having extraordinary tyrosinase activity, the radioactive copper will within a very short time accumulate at such tumor site either by being substituted for the copper which is already present at the site or by being incorporated into new tyrosinase formation. By means of an appropriate scanning device one can determine exactly where the radioactive copper is maximized. If the scan shows a maximization of the copper at the tumor site, then this is a definite indication that this particular tumor is treatable by the compounds of the present invention. When there is an unusual accumulation of copper at the tumor, the compounds of the present invention will accumulate at the tumor site, due to the presence of copper-chelating penicillamine therein, and exert its action directly at the site of the tumor.

The copper isotope which would be best suited for this purpose is $^{64}Cu$ which has a half life of about 12.7 hours. The radioisotope may be administered as any water-soluble copper salt which exerts no toxic effects at the dose administered. Because radioactive scanners are now being made which are extremely sensitive, only very small amounts of radioactive copper need be administered. The recommended daily allowance for copper is 2 mg. The amount of radioactive copper which need be administered to have an appropriate amount of radiation to be scannable is much smaller than 2 mg and may easily be emperically determined without undue experimentation.

This method of diagnosis using radioactive copper may also be used to diagnose the presence of a malignancy in the early stages of certain tumors. It is known that many categories of tumors have extremely high tyrosinase activity, including melanoma, breast carcinoma, rectal carcinoma, Hodgkin's disease, hepatic carcinoma, endometrial carcinoma, carcinoma of the larynx, carcinoma of the mouth, lymphocarcinoma, carcinoma of the tonsil and neurofibrosarcoma. If radioactive copper is administered to persons suspected of having any of these tumors and the radioactivity accumulates at the suspected site of the tumor, then this will be a positive indication of the presence and location of the malignancy and its metastases. The use of this radioactive copper test is also useful for monitoring the treatment by means of the present invention and determining the necessity of follow up treatment by any other means.

DETAILED DESCRIPTION OF PREFERRED EMBODIMENTS

The preferred compound used in the composition and method of the present invention is prepared by the reaction of benzaldehyde with penicillamine. The reaction may take place in any appropriate solvent for the two reactants, which are preferably stirred together in the solvent in equimolar amounts.

This compound and reaction are known in the prior art as for example in the publications of Nagasawa, H. T. et al, *J. Heterocyclic Chem.*, 18, 1047 (1981) and Vestling M. M. et al, *J. Heterocyclic Chem.*, 12, 243 (1975). See also Pesek J. J. et al, *Tetrahedron* 31, 907 (1975) and Terol, A. et al *Eur. J. Med. Chem.-Chimica Therapeutica*, 13, 149 (1978).

None of the prior publications disclosing this compound discloses any kind of pharmaceutical utility therefor. In the Terol et al publication, this compound and other related compounds were tested for pharmaceutical utility as radio-protectant agents. The publication discloses however that 5,5-dimethyl-2-phenyl-4-thiazolidine carboxylic acid has absolutely no effect whatsoever as a radio-protectant agent. Its $LD_{50}$ is disclosed therein as being 1200 mg/kg.

The preferred method of administration of the compound of the present invention is intravenously (or intra-arterially), in the form of its alkali metal or ammonium salt or other water-soluble pharmaceutically acceptable salt. It can also be administered in any other appropriate manner including orally, intramuscularly, vaginally or rectally.

The estimated dosage range for administration of this compound is about 25 to about 600 mg/kg/day. Below about 25 mg/kg the effects of the compound become minimal. Even less can be used if such minimal effects are acceptable. The maximum dosage of 600 mg/kg is one half of the $LD_{50}$. Generally, the use of smaller dosages is sufficient. The preferred dosage is about 33-200 mg/kg/day. When administered intravenously it is preferably administered to the artery that leads to the tumor as a continuous drip.

When formulated in a pharmaceutical composition the active principle may be combined with any pharmaceutically acceptable excipient as is well known in the art. For example, injectable preparations may be prepared by forming solutions and/or suspensions in any of the usual sterile media, which may be oily or aqueous. Preferably the 5,5-dimethyl-2-phenyl-4-thiazolidine carboxylic acid is prepared in the form of an alkali metal or ammonium salt so as to become water soluble. It is to be understood, however, that the active compound may be administered as the acid or in the form of any pharmaceutically acceptable salt or ester, such as a methyl or ethyl ester.

When preparing for oral administration, powders, tablets, capsules, syrups and elixers may be formed using conventional pharmaceutical vehicles, all as is well known in the art.

The compounds in accordance with the present invention which are the reaction products of penicillamine with aldehydes other than benzaldehyde are made and used in a manner analogous to that discussed above with respect to benzaldehyde. Those skilled in the art will be able to determine the exact parameters of the synthesis reactions and the preferred dosages by standard emperical methods without undue experimentation.

EXAMPLE 1: Preparation of 5,5-Dimethyl-2-Phenyl-4-Thiazolidine Carboxylic Acid One mole of benzaldehyde was dissolved in 100 cc of 90% ethanol with continuous stirring. One mole of penicillamine was dissolved in water with continuous stirring. The two solutions were then mixed together while stirring was continued. The solution was left to stand at room temperature. Within 15 minutes, a white precipitate occurred. The white precipitate was washed with distilled water through sintered glass. The washed precipitate was then dryed at 100° C. to obtain crystals.

EXAMPLE 2: Formulation

An intravenous (or intra-arterial) drip composition may be prepared by dissolving one unit dose of the sodium salt of 5,5-dimethyl-2-phenyl-4-thiazolidine carboxylic acid (i.e. about 33-100 mg/kg) in a liter of physiological saline solution.

EXAMPLE 3: Mode of Administration

A patient having a tumor suspected to have substantial tyrosinase activity is injected with a composition containing a radioactive copper salt. The salt may be $^{64}CuSO_4$. The dosage should be such as to provide a scannable amount of radioactivity without being harmful to the patient. If the patient shows an accumulation of radioactivity at specific sites upon full body scan (such as a CAT scan), this will indicate areas of high tyrosinase activity and will indicate that the patient is a candidate for treatment in accordance with the present invention.

If the patient is shown to be a candidate for the present treatment by means of the radioactive copper diagnostic test, or by any other diagnostic method such as analysis of a surgically removed biopsy of the tumor for tyrosinase activity, then an intra-arterial drip of about 33-100 mg/kg of the sodium salt of 5,5-dimethyl-2-phenyl-4-thiazolidine carboxylic acid in about one liter of physiological saline is begun, preferably into an artery leading to the tumor site as identified in the full body scan.

The administration is continued daily for about one week at which time another administration of radioactive copper and full body scan takes place in order to analyze the results of the treatment. The treatment should continue until there is no more indication of tumor activity.

Experimental

Thirty-seven black mice were divided into two groups. Group I had 18 mice and was the control group. Group II had 19 mice and was the treated group. Each mouse was innoculated with 100,000 mouse melanoma cells subcutaneously. After the tumor was palpable (after about a week) the control group received saline orally. The treated group got 33 mg/kg of 5,5-dimethyl-2-phenyl-4-thiazolidine carboxylic acid every day by oral intubation. All of the control group died within an average of twenty-three days. The treated group started dying at day 50. The last mouse of the treated group died on day 70. The treated group died from day 50 on at the rate of about one mouse per day. The tumors in the treated group developed slower than the tumors in the control group. Two mice in the treated group survived cured. The tumor disappeared in the two cured mice.

The same experiment was repeated with 20 control mice and 20 mice in the treated group, employing doses of 5,5-dimethyl-2-phenyl-4-thiazolidine carboxylic acid at 100 mg/kg. The treatment began about one day after innoculation. The control group died at the same time as the control group in the previous experiment. The treated group developed no palpable tumors. Five of the treated mice died between the 7th and 9th day. The reasons for these deaths are unclear, but it is presumed that they were asphyxiated by intubation.

It will be obvious to those skilled in the art that various changes may be made without departing from the scope of the invention and the invention is not to be considered limited to what is described in the specification. For example, any tumor which is shown to have high tyrosinase activity or which is indicated to be treatable by means of the diagnostic test described herein may be treated by means of the compounds of the present invention. The specific dosages, while generally indicated herein, can be determined for specific compounds, formulations and modes of administration, and for the specific patient without undue experimentation. Additionally, specific vehicles and excipients form no part of the present invention and would be well known to those ordinarily skilled in this art once the compounds of the present invention and their modes of action are made known to them.

What is claimed is:

1. A composition for inhibiting the growth of tumors having high tyrosinase activity, comprising an effective amount of an active principle comprising 5,5-dimethyl-2-phenyl-4-thiazolidine carboxylic acid, or a pharmaceutically acceptable salt or ester thereof, and a pharmaceutically acceptable vehicle selected from the group consisting of an oily vehicle chosen so as to permit administration in the form of an injectable solution or suspension, a vehicle chosen to permit administration in oral dosage form, and a vehicle chosen so as to permit administration as an intravenous drip.

2. A composition in accordance with claim 1 in the form of an injectable solution or suspension in an oily pharmaceutically acceptable vehicle.

3. A composition in accordance with claim 1 in oral dosage form.

4. A composition in accordance with claim 3 in the form of a unit dosage capsule or tablet.

5. A composition in accordance with claim 1 wherein said vehicle is chosen so as to permit administration as an intravenous drip.

6. A composition in accordance with claim 1 wherein said active principle is 5,5-dimethyl-2-phenyl-4-thiazolidine carboxylic acid,.

7. A composition for inhibiting the growth of tumors having high tyrosinase activity, comprising an effective amount of an active principal which is a pharmaceutically acceptable salt or ester of 5,5-dimethyl-2-phenyl-4-thiazolidine carboxylic acid, and a pharmaceutically acceptable vehicle.

8. A composition in accordance with claim 7 in the form of an injectable solution, said 5,5-dimethyl-2-phenyl-4-thiazolidine carboxylic acid being in the form of the alkali metal or ammonium salt thereof in aqueous solution.

9. A composition for inhibiting the growth of tumors having high tyrosinase activity, comprising an effective amount of an active principal which is a pharmaceutically acceptable salt or ester of 5,5-dimethyl-2-(2-hydroxyphenyl)-4-thiazolidine carboxylic acid, or a pharmaceutically acceptable salt or ester thereof, and a pharmaceutically acceptable vehicle.

10. A composition in accordance with claim 9 in the form of an injectable solution or suspension in an oily pharmaceutically acceptable vehicle.

11. A composition in accordance with claim 9 in the form of an injectable solution, said 5,5-dimethyl-2-(2-hydroxyphenyl)-4-thiazolidine carboxylic acid being in the form of the alkali metal or ammonium salt thereof in aqueous solution.

12. A method for inhibiting the growth of melanoma tumors having high tyrosinase activity, comprising administering 5,5-dimethyl-2-phenyl-4-thiazolidine carboxylic acid, or a pharmaceutically acceptable salt or ester thereof, to a patient having a melanoma tumor, in an amount effective to inhibit tumor growth.

13. A method for inhibiting the growth of tumors having high tyrosinase activity, comprising administering 5,5-dimethyl-2-phenyl-4-thiazolidine carboxylic acid or a pharmaceutically acceptable salt or ester thereof, to a patient in an amount effective to inhibit tumor growth.

14. A method for inhibiting the growth of tumors having high tyrosinase activity, comprising administering 5,5-dimethyl-2-(2-hydroxyphenyl)-4-thiazolidine carboxylic acid or a pharmaceutically acceptable salt or ester thereof, to a patient in an amount effective to inhibit tumor growth.

* * * * *